May 20, 1958 I. J. HAWKERSMITH Plant Pat. 1,710
DOGWOOD PLANT
Filed Oct. 7, 1957
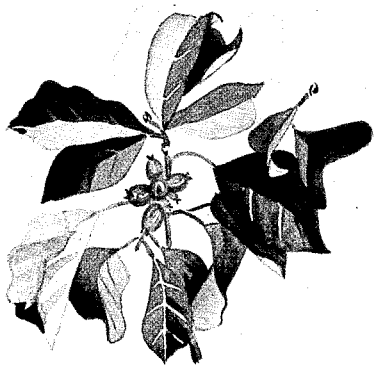
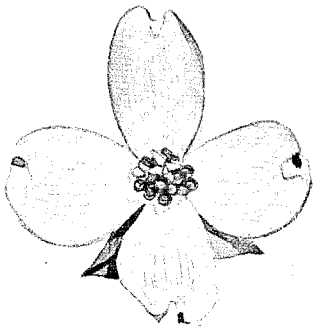
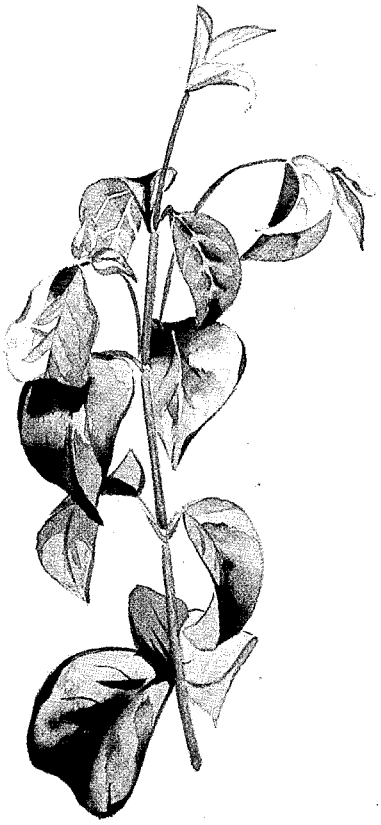
INVENTOR
Isaac J. Hawkersmith
BY
Lamont Johnston
ATTORNEY United States Patent Office Plant Pat. 1,710
Patented May 20, 1958

1,710

DOGWOOD PLANT

Isaac J. Hawkersmith, Winchester, Tenn.

Application October 7, 1957, Serial No. 688,797

1 Claim. (Cl. 47—59)

This invention is a new and improved red flowering dogwood plant and is particularly noted for the Spiraea Red bracts and distinct Magenta Rose colored young leaves and vigorous shoots. Lower leaves on growing shoots are also distinctly suffused with Magenta Rose.

This cultivar is the result of a chance seedling grown from a seed of *Cornus florida* rubra in a nursery near Sweetwater, Tennessee. Budwood obtained from the original tree has been asexually reproduced by budding and grafting in Franklin County, Tennessee.

The accompanying illustration shows a typical flowering bract, the new growth, and a typical fruit cluster.

Color plate references in the following detailed description indicate "Horticultural Colour Chart" by The British Colour Council. Where there are other references to color, the ordinary dictionary meanings of the terms are intended.

*The plant*

Growth habits: Very vigorous under good growing conditions and shows indication of being more drought resistant than the common pink flowering dogwood. It is also a good propagator.

Blooming habits: This cultivar by careful comparison, when grown under comparable conditions, flowers at the same time as the common pink flowering dogwood. However, it has been noted that less fading occurs with the bracts with age.

Branches: Branching habit resembles the common pink flowering dogwood but is more vigorous and has a distinct lighter color or bloom which is noticeable at all seasons.

Foliage: New tip foliage is Spinach Green o960/1, suffused or masked with Magenta Rose o27/2 and covered with a heavy bloom or white pubescence giving a silvery rose color. Under side of new tip leaves are entirely Magenta Rose o27/2 with a heavy bloom.

On vigorous growing shoots the 2nd pair of leaves are Spinach Green o960/1 suffused with Magenta Rose o27/2 near the base and margin of the leaf with bloom still present. Under side of leaves are Magenta Rose o27/2 suffused with green and bloom.

On vigorous growing shoots the 3rd pair of leaves are Spinach Green o960/1 with light suffusion of Magenta Rose and still with a bloom.

Mature leaves are Spinach Green o960/1 decidedly covered with bloom which gives a silvery green color. Lower surface of mature leaves are Fern Green o862 heavy covered with a white bloom.

In comparison, the common pink flowering dogwood when grown under comparable conditions has only the Magenta Rose pigment suffused with the green on tip leaves and is not present in older leaves.

*Flowers*

The bloom bracts are distinctly outstanding, being a Spiraea Red o25 color with very little to no fading noticed at anthesis. In comparison to the common pink flowering dogwood, they are both the same size, usually measuring 3 to 4 inches across.

The basal portion of the bracts are white, quickly suffusing into the Spiraea Red. The apical end of the bract has a small white tip blending into the reddish brown notch or tip. The disc flowers in the center are similar in color to the common pink flowering dogwood. The bracts are broad obovate in outline with the typical notch of the apical end.

*Fruit*

It was noted under identical growing conditions that this new cultivar has more fruit set and more fruit per cluster than the common pink flowering dogwood. The individual drupes are Cardinal Red 822 in color.

I claim:

A new and distinct variety of dogwood plant substantially as herein shown and described, characterized particularly by its Spiraea Red bracts and Magenta Rose colored young leaves and with lower green leaves also distinctly suffused with Magenta Rose.

No references cited.